United States Patent
Kraft et al.

(10) Patent No.: US 8,685,101 B2
(45) Date of Patent: Apr. 1, 2014

(54) IMPLANT WITH COMPLIANT LAYER

(75) Inventors: Markus Kraft, Frenkendorf (CH); Jayr Bass, Basel (CH); Roger Berger, Vienna (CH)

(73) Assignee: DePuy Synthes Products, LLC, Raynham, MA (US)

(*) Notice: Subject to any disclaimer, the term of this patent is extended or adjusted under 35 U.S.C. 154(b) by 0 days.

(21) Appl. No.: 13/269,812

(22) Filed: Oct. 10, 2011

(65) Prior Publication Data
US 2013/0090733 A1 Apr. 11, 2013

(51) Int. Cl.
*A61F 2/44* (2006.01)
(52) U.S. Cl.
USPC ............................ 623/17.16; 623/17.11
(58) Field of Classification Search
USPC ............................. 623/17.11, 17.16
See application file for complete search history.

(56) References Cited

U.S. PATENT DOCUMENTS

| | | | |
|---|---|---|---|
| 4,946,378 A * | 8/1990 | Hirayama et al. | 623/17.16 |
| 5,320,644 A | 6/1994 | Baumgartner | |
| 5,545,229 A | 8/1996 | Parsons et al. | |
| 6,368,350 B1 | 4/2002 | Erickson et al. | |
| 6,395,033 B1 | 5/2002 | Pepper | |
| 6,533,818 B1 * | 3/2003 | Weber et al. | 623/17.16 |
| 6,749,635 B1 | 6/2004 | Bryan | |
| 7,208,222 B2 | 4/2007 | Rolfe et al. | |
| 7,563,284 B2 | 7/2009 | Coppes et al. | |
| 7,601,174 B2 | 10/2009 | Kelly et al. | |
| 7,776,092 B2 | 8/2010 | Lee et al. | |
| 2004/0106995 A1* | 6/2004 | Le Couedic et al. | 623/17.11 |
| 2005/0112397 A1 | 5/2005 | Rolfe et al. | |
| 2005/0143824 A1 | 6/2005 | Richelsoph et al. | |
| 2005/0154468 A1 | 7/2005 | Rivin | |
| 2005/0165485 A1* | 7/2005 | Trieu | 623/17.13 |
| 2005/0246021 A1 | 11/2005 | Ringeisen et al. | |
| 2005/0256581 A1* | 11/2005 | Songer et al. | 623/17.16 |
| 2006/0276900 A1 | 12/2006 | Carpenter | |
| 2006/0282166 A1 | 12/2006 | Molz et al. | |
| 2007/0073403 A1 | 3/2007 | Lombardo et al. | |
| 2008/0161919 A1 | 7/2008 | Melkent | |
| 2008/0161928 A1 | 7/2008 | Trieu | |

(Continued)

FOREIGN PATENT DOCUMENTS

| | | |
|---|---|---|
| DE | 2263842 A1 | 7/1974 |
| EP | 0317972 A1 | 5/1989 |

(Continued)

OTHER PUBLICATIONS

Notification of Transmittal of the International Search Report, dated Dec. 14, 2012, received in connection with corresponding International patent application No. PCT/US2012/059438.

*Primary Examiner* — Christian Sevilla
(74) *Attorney, Agent, or Firm* — Meunier Carlin & Curfman, LLC (57) ABSTRACT

An intervertebral spacer having an upper layer, a lower layer and at least one non-planer compliant layer. The non-planer compliant layer is disposed between the lower layer and the upper layer and includes a portion that extends outside a lateral plane in which the compliant layer resides. The non-planar compliant layer made of a material that is more yielding than the upper layer and the lower layers, and may have a cross-section that is z-shaped, u-shaped, sinusoidal-shaped, zigzag shaped, etc.

16 Claims, 5 Drawing Sheets

(56) References Cited

U.S. PATENT DOCUMENTS

| | | |
|---|---|---|
| 2008/0183292 A1 | 7/2008 | Trieu |
| 2009/0036987 A1* | 2/2009 | Oh et al. .................... 623/17.16 |
| 2009/0076609 A1 | 3/2009 | Stewart |
| 2009/0076614 A1 | 3/2009 | Arramon |
| 2009/0093885 A1 | 4/2009 | Levieux et al. |
| 2009/0292363 A1 | 11/2009 | Goldfarb et al. |
| 2009/0326657 A1 | 12/2009 | Grinberg et al. |
| 2010/0030338 A1 | 2/2010 | Simon |
| 2010/0217397 A1 | 8/2010 | Pointillart et al. |
| 2010/0280550 A1 | 11/2010 | Reo et al. |
| 2010/0292799 A1 | 11/2010 | Hansell et al. |
| 2011/0071635 A1 | 3/2011 | Zhang et al. |
| 2012/0035731 A1 | 2/2012 | Lazennec et al. |

FOREIGN PATENT DOCUMENTS

| | | |
|---|---|---|
| EP | 1287794 A1 | 3/2003 |
| EP | 1287795 A1 | 3/2003 |
| EP | 1818024 A1 | 8/2007 |
| FR | 2894808 A1 | 6/2007 |
| FR | 2942131 A1 | 8/2010 |
| WO | 03003952 A1 | 1/2003 |
| WO | 2004052234 A2 | 6/2004 |
| WO | 2006078662 A1 | 7/2006 |
| WO | 2006078663 A2 | 7/2006 |
| WO | 2007077319 A2 | 7/2007 |
| WO | 2009055160 A2 | 4/2009 |
| WO | 2009145766 A1 | 12/2009 |
| WO | 2010088766 A1 | 8/2010 |
| WO | 2010100267 A1 | 9/2010 |

* cited by examiner

IMPLANT WITH COMPLIANT LAYER

BACKGROUND

The spine is comprised of twenty-four vertebrae that are stacked one upon the other to form the spinal column. The spine provides strength and support to allow the body to stand and to provide flexibility and motion. Each vertebra includes an opening through which the spinal cord passes enabling the spine to protect the spinal cord.

Between each pair of vertebrae is an intervertebral disc. The disc is composed of three component structures: (1) the nucleus pulposus; (2) the annulus fibrosus; and (3) the vertebral endplates. The disc serves several purposes, including absorbing shock, relieving friction, and handling pressure exerted between the superior and inferior vertebral bodies associated with the disc. The disc also absorbs stress between the vertebral bodies, which stress would otherwise lead to degeneration or fracture of the vertebral bodies.

Disorders of the spine are some of the costliest and most debilitating health problems facing the populations of the United States and the rest of the world, costing billions of dollars each year. Moreover, as populations of developed countries continue to age, the incidence of spinal disorders will continue to grow. Typical disorders include those caused by degeneration, trauma, genetic disorders, or other causes.

SUMMARY

Various embodiments disclosed herein pertain to intervertebral spacers having at least one non-planar compliant layer. The shape and footprint of the intervertebral spacers may vary in accordance with intended use. The intervertebral spacers may include upper and lower layers having holes or a solid structure. If included, the holes may be square, rectangular, circular, kidney shaped, or any other shape to accept a bone graft, bone chips or bone substitution material. Further, any number of holes may be provided. The non-planar compliant layer may comprise an implantable, biocompatible elastic or foamed material that is more yielding than that of the upper layer and the lower layers.

In accordance with some implementations, there is provided an intervertebral spacer that includes an upper layer having a first exterior surface and a first interior surface and a lower layer having a second exterior surface and a second interior surface. A non-planar compliant layer is substantially disposed between the first interior surface of the upper layer and the second interior surface of the lower layer. The first interior surface of the upper layer and the second interior surface of the lower layer each have a predetermined complementary shape to receive the non-planar compliant layer. The upper layer and lower layer comprise a first biocompatible material, and the non-planar compliant layer comprises a second biocompatible material is more yielding than the first biocompatible material.

In accordance with some implementations, there is provided an intervertebral spacer that includes an upper layer, a lower layer, and a non-planar compliant layer substantially disposed between and engaging at least a portion of the upper layer and at least a portion of the lower layer. The engagement of the non-planar compliant layer with the at least a portion of the upper layer and the at least a portion of the lower layer provides resistance to shear forces that act on the intervertebral spacer. The upper layer and lower layer comprise a first biocompatible material, and wherein the non-planar compliant layer comprises a second biocompatible material.

In accordance with some implementations, there is provided a multilayer intervertebral spacer that includes a lower layer having a first engagement region, an upper layer having a second engagement region, and at least one intermediate non-planar layer having a portion thereof extending outside a lateral plane of the intervertebral spacer in which the at least one intermediate non-planar layer is disposed. The at least one intermediate layer engages the first engagement region and the second engagement region. The at least one intermediate non-planar layer comprises a biocompatible material that is more yielding than that of the lower layer and the upper layer.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

To facilitate an understanding of and for the purpose of illustrating the present disclosure, exemplary features and implementations are disclosed in the accompanying drawings, it being understood, however, that the present disclosure is not limited to the precise arrangements and instrumentalities shown, and wherein similar reference characters denote similar elements throughout the several views, and wherein.

DETAILED DESCRIPTION

Certain terminology is used in the following description for convenience only and is not limiting. The words "right", "left", "lower", and "upper" designate direction in the drawings to which reference is made. The words "inner", "outer" refer to directions toward and away from, respectively, the geometric center of the described feature or device. The words "distal" and "proximal" refer to directions taken in context of the item described and, with regard to the instruments herein described, are typically based on the perspective of the surgeon using such instruments. The words "anterior", "posterior", "superior", "inferior", "medial", "lateral", and related words and/or phrases designate preferred positions and orientation in the human body to which reference is made. The terminology includes the above-listed words, derivatives thereof, and words of similar import.

In addition, various components may be described herein as extending horizontally along a longitudinal direction "L" and lateral direction "A", and vertically along a transverse direction "T". Unless otherwise specified herein, the terms "lateral", "longitudinal", and "transverse" are used to describe the orthogonal directional components of various items. It should be appreciated that while the longitudinal and lateral directions are illustrated as extending along a horizontal plane, and that the transverse direction is illustrated as extending along a vertical plane, the planes that encompass the various directions may differ during use. Accordingly, the directional terms "vertical" and "horizontal" are used to describe the components merely for the purposes of clarity and illustration and are not meant to be limiting.

Figure 1:
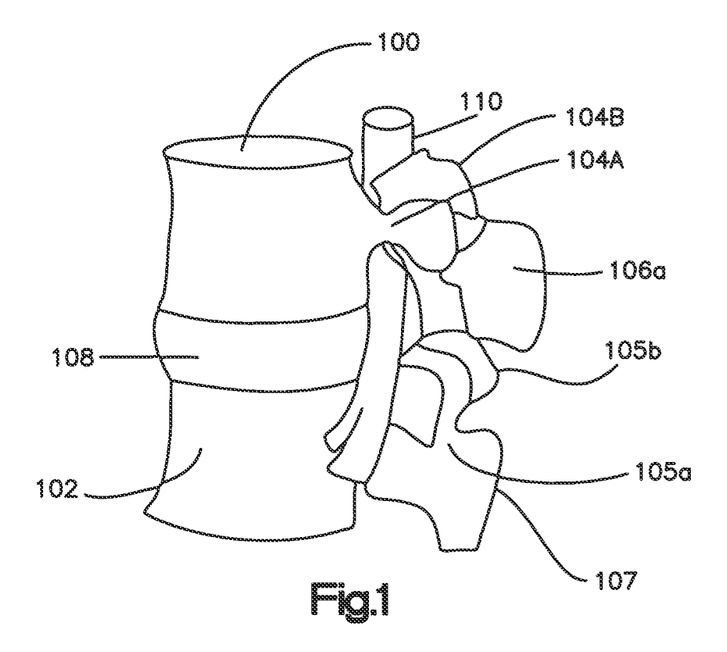
FIG. 1 is a lateral view of a pair of adjacent vertebral bodies.

FIG. 1 illustrates a pair of adjacent vertebrae, including a superior or upper vertebral body 100 and an inferior or lower vertebral body 102. The upper vertebral body 100 includes a pair of transverse processes 104a, 104b and a spinous process 106 extending generally posteriorly. The lower vertebral body 102 includes a pair of transverse processes 105a, 105b and a spinous process 107. A disc 108 is located between the superior vertebral body 100 and the inferior vertebral body 102. The spinal cord 110 extends through a central passage formed by the spinal column.

When the disc is damaged due to disc degeneration, trauma, or other disorder, the disc between the superior vertebral body 100 and the inferior vertebral body 102 may collapse. This result also commonly occurs when the vertebral bodies are afflicted with disc degeneration or are fractured or otherwise damaged.

Figure 2:
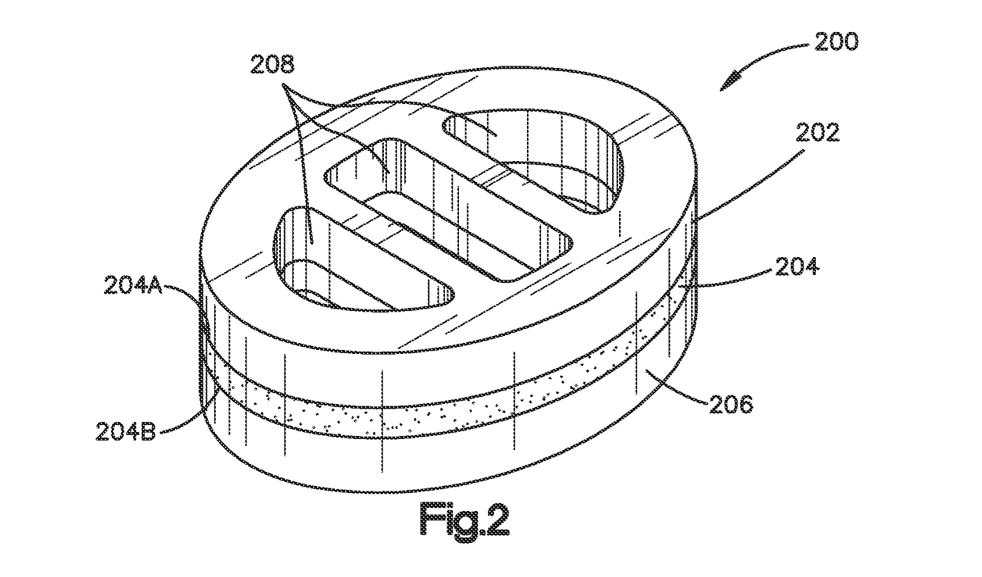
FIG. 2 is a perspective view of an intervertebral spacer.

Referring now to FIG. 2, there is shown a perspective view of an intervertebral spacer 200. The intervertebral spacer 200 may include three layers, for example, a superior endplate as an upper layer 202, an inferior endplate as a lower layer 206, and a compliant layer 204. The upper layer 202 and the lower layer 206 may define several holes 208 in which bone can build a bridge from the superior to the inferior vertebral bodies. The holes 208 may be filled with a bone graft or other bone substitution material.

The compliant layer 204 of the intervertebral spacer 200 is a planar layer, i.e., the layer is provided substantially within planes that define an upper surface 204A and a lower surface 204B of the compliant layer 204. With such a structure, there is a risk of disintegration of the intervertebral spacer 200 due to shear forces acting on the spacer. The shear forces exist because the space where the disk 108 resides is not horizontal, but tilted in the anteroposterior (AP) direction and the spacer 200, once implanted in the spine 100, the spacer 200 bears the load from the portion of the spinal column above the spacer. The amount of the load depends on the placement of the spacer 200 within the spinal column. This load consists of two components with the compressive component (acting in vertical direction onto the endplate of the vertebral body) and the shear component.

To remediate the effects of shear, in accordance with aspects of the present disclosure, the compliant layer may be provided as non-planar layer. The non-planer layer provides built-in resistance to shear whereas a planar layer, such as the compliant layer 204 does not. Thus, representative embodiments of an intervertebral spacer having a non-planar compliant layer will now be discussed with reference to FIGS. 3-12.

In FIGS. 3-12 the general shape of the disclosed intervertebral spacers may vary in accordance with intended use. For example, for use in the lumbar region, the intervertebral spacer may be oval-shaped, kidney-shaped or rectangular, etc. In some implementations, the intervertebral spacer may be split into two sections for placement in the body from the posterior, where the two sections are introduced from each side of the body. For use in the cervical region, the intervertebral spacer may be a trapezoidal shape with rounded edges.

The disclosed intervertebral spacers may include upper and lower layers having holes or a solid structure. If included, the holes may be square, rectangular, circular, kidney shaped, or any other shape to accept a bone graft, bone chips or bone substitution material. Further, any number of holes may be provided.

The non-planar compliant layer of the intervertebral spacers of FIGS. 3-12 may comprise one or more of the following implantable, biocompatible elastic or foamed materials. For example, the non-planar compliant layer may comprise polyurethane, silicone, co-polymers of polyurethane, co-polymers of silicone, and polyolefin. In some implementations, the compliant layer may be made of a polymer material that cures in situ or that hardens over time. In some cases the compliant layer may be made of polymer fibers which form a felt like structure, a woven structure or a knitted structure. Polymer fibers may consist out of any suitable biocompatible material, e.g. PAEK, PEEK, PEKK, PEK, PET, PE, Ultra-high-molecular-weight polyethylene (UHMWPE), etc. It is noted that the non-planar compliant layer is not limited to the above materials, as these are being provided for exemplary purposes. Although the example intervertebral spacers of FIGS. 3-12 illustrate continuous non-planar compliant layers comprised of the materials above, in some implementations, the non-planar compliant layer may be interrupted in the anteroposterior (AP) or lateral directions such that a gap is present in the non-planar compliant layer.

The upper layer and lower layer of the intervertebral spacers of FIGS. 3-12 may be made from metal (cobalt chrome, steel, titanium, titanium alloy, tantalum, zirconium, niobium, or nitinol), ceramic (alumina, zirconia and mixtures thereof (ATZ or ZTA), or silicon nitride), or a polymer (Polyaryletherketone (PAEK), polyether ether ketone (PEEK), polyether ketone ketone (PEKK), Poly Ether Ketone (PEK), or polyether ketone ether ketone ketone (PEKEKK), Poly methyl methacrylate (PMMA), a carbon reinforced PAEK, or polyethylene). It is noted that the upper and lower layers are not limited to the above materials, as these are being provided for exemplary purposes. Thus, in the intervertebral spacers of FIGS. 3-12, the non-planar compliant layer is made of a material that is more yielding than the upper layer and the lower layers.

In some implementations, the intervertebral spacers of FIGS. 3-12 are provided as a pre-assembled unit. The intervertebral spacers are intended to be inserted between two vertebrae and anchored on the vertebral plates. The intervertebral spacers may be fixed to bone through a variety of techniques, such as including pyramids, spikes, grooves, etc., on the upper and lower surface of the upper layer and lower layer, respectively.

The intervertebral spacers of FIGS. 3-12 generally have a width of 8 to 20 mm, a height of 4 to 15 mm and a depth of 8 to 20 mm (cervical), or a width of 6 to 60 mm, a height of 6 to 25 mm, and a depth of 20 to 50 mm (thoracolumbar). As such, the intervertebral spacer has dimensions suitable for being installed by anterior, anterolateral, direct lateral, posterior, or posterolateral access. The non-planar compliant layer, of a suitable thickness, is capable of reproducing the articulation movements. The non-planar compliant layer thus has a height to allow the preferred maximum ranges required by the anatomical movements. For example, the non-planar compliant layer may have a thickness of 1 to 8 mm (cervical) or 2 to 12 mm (lumbar).

Figure 3A:
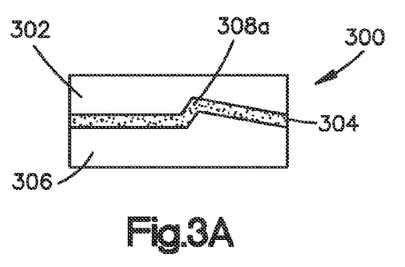
FIGS. 3A and 3B are side views of an intervertebral spacer in accordance with a first embodiment.
Figure 3B:
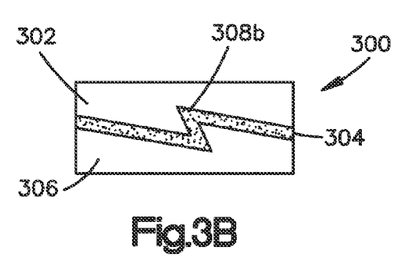

With the general introduction above to the intervertebral spacers of FIGS. 3-12, specific embodiments will now be described. Referring to FIGS. 3A and 3B, there are side views of an intervertebral spacer 300 in accordance with a first embodiment. As shown, a non-planar compliant layer 304 has a generally "z-shaped" cross section. An upper layer 302 and a lower layer 306 may define holes or may include solid surfaces. The upper layer 302 and the lower layer 306 include interior surfaces having a complementary shape to the z-shaped non-planar compliant layer 304. The spacer of FIGS. 3A and 3B provide for bending in AP and lateral direction. A bend 308a in the compliant layer of FIG. 3A is less pronounced than a bend 308b in the spacer of FIG. 3B in order to provide different levels of resistance to shear. The bends 308a and 308b may have varying degrees of severity in order to provide a desired resistance to shear.

Figure 4A:
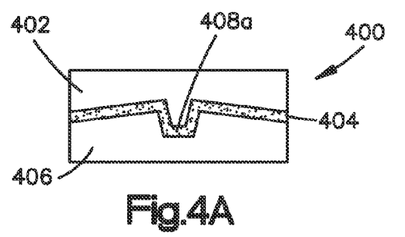
FIGS. 4A and 4B illustrate an intervertebral spacer in accordance with a second embodiment.
Figure 4B:
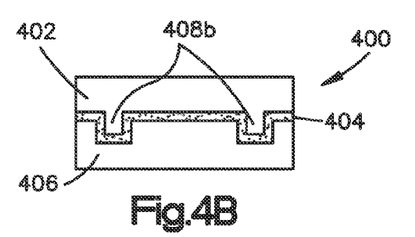

Referring now to FIGS. 4A and 4B, there is shown an intervertebral spacer 400 in accordance with a second embodiment. As shown, a cross-section of a non-planar compliant layer 404 has a "u-shaped" section (408a) or "u-shaped" sections (408b) along the sides of the intervertebral spacer 400. An upper layer 402 and a lower layer 406 may be solid or may define holes, and include interior surfaces that are complementary to the u-shaped sections 408a and 408b. The non-planar u-shaped compliant layers 404 of FIG. 4A and FIG. 4B offer different levels of resistance to shear, as well as torsion. The spacer 400 of FIGS. 4A and 4B provides for bending in AP and lateral direction, however torsion is restricted. In particular, the spacer of FIG. 4B is offers more torsional constraint that that of FIG. 4A because of the addition u-shaped portion 408b.

Figure 5A:
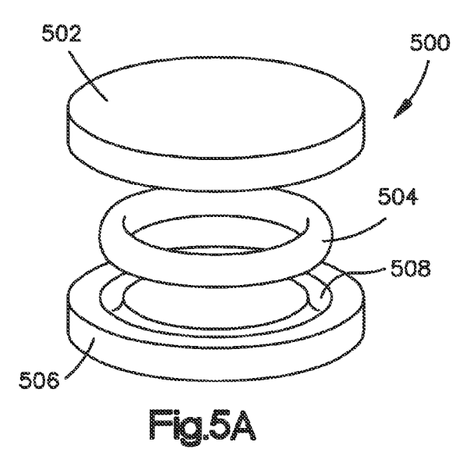
FIGS. 5A and 5B illustrate a perspective and cross-sectional view an intervertebral spacer in accordance with a third embodiment.
Figure 5B:
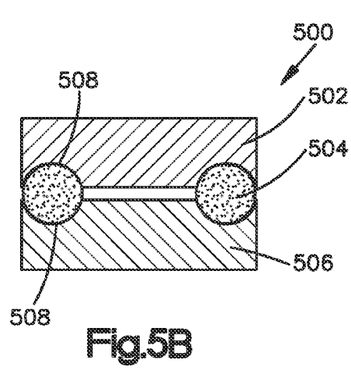

Referring to FIGS. 5A and 5B, there is shown a perspective and cross-sectional view an intervertebral spacer 500 in accordance with a third embodiment. As shown, the intervertebral spacer 500 is generally circular; however the intervertebral spacer 500 may have other shapes. The non-planar compliant layer 504 is shaped as a ring and is positioned between an upper layer 502 and a lower layer 506. As best shown in FIG. 5B, the non-planar compliant layer 504 is shaped as an o-ring and is positioned between the upper layer 502 and lower layer 504. Each of the upper and lower layers 502 and 504 has a channel 508 to receive the non-planar compliant layer 504. With regard to other shapes, for example, if the intervertebral spacer 500 is rectangular, the compliant layer 504 is rectangular, etc.

Figure 6:
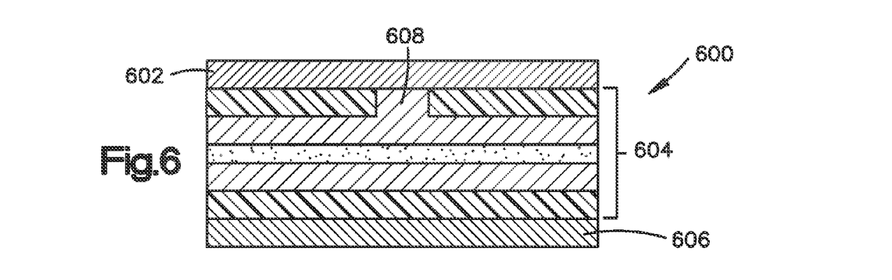
FIG. 6 illustrates a cross-sectional view of an intervertebral spacer in accordance with a fourth embodiment.

Referring to FIG. 6, there is shown a cross-sectional view of an intervertebral spacer 600 in accordance with a fourth embodiment. The intervertebral spacer 600 includes plural compliant layers 604 that are disposed between an upper layer 602 and a lower layer 606. Any number of compliant layers 604 may be provided from the list of materials noted above to achieve a desired height and/or overall compliance. At least one of the compliant layers 604 includes a non-planar portion 608.

Figure 7:
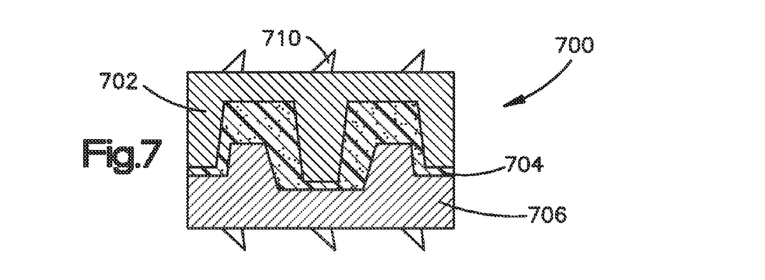
FIG. 7 illustrates an intervertebral spacer in accordance with a fifth embodiment.

Referring now to FIG. 7, there is shown an intervertebral spacer 700 in accordance with a fifth embodiment. As shown, the non-planar compliant layer 704 has a cross-section that is a continuous "u-shape" along the sides of the intervertebral spacer 700. An upper layer 702 and a lower layer 706 each may include spikes 710 (or other mechanism) to fasten the intervertebral spacer 700 to the vertebral bodies.

Figure 8A:
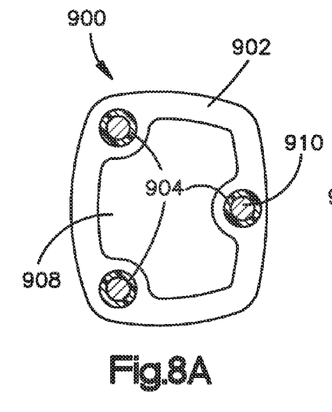
FIGS. 8A and 8B illustrate a top view and side view of an intervertebral spacer in accordance with a seventh embodiment.
Figure 8B:
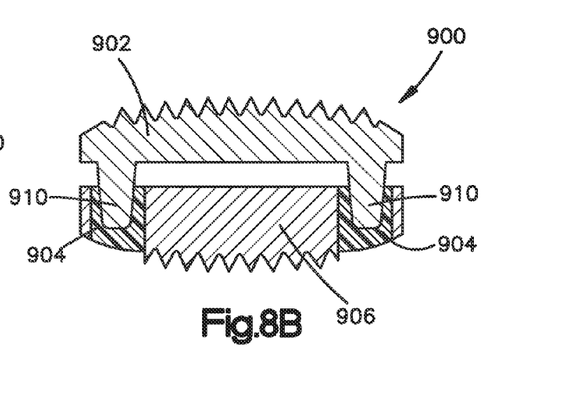

Referring to FIGS. 8A and 8B, there is shown a top view and a side view of an intervertebral spacer 900 in accordance with a sixth embodiment. As shown, the intervertebral spacer 900 is generally circular. A non-planar compliant layer comprises three elastic islands 904 positioned between an upper layer 902 and a lower layer 906. The upper layer 902 and lower layer 906 each define an open area 908 that is in the central portion of the intervertebral spacer 900. As shown in FIG. 9B, the elastic islands 904 each respectively receive an integral protrusion 910 of the upper layer 902.

Figure 9:
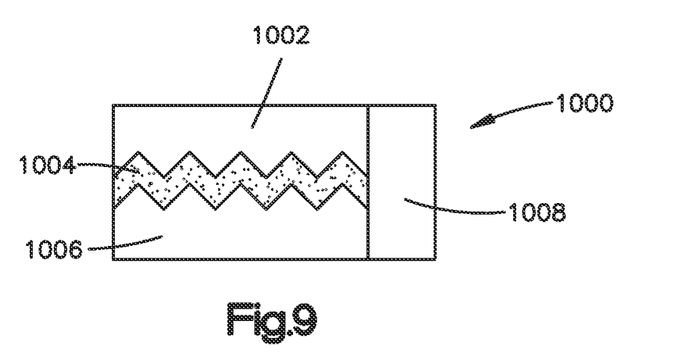
FIG. 9 illustrates an intervertebral spacer in accordance with an eighth embodiment.

Referring now to FIG. 9, there is shown an intervertebral spacer 1000 in accordance with an seventh embodiment. As shown, a non-planar compliant layer 1004 has a "saw-tooth" cross-section along the sides of the intervertebral spacer 1000. An upper layer 1002 and a lower layer 1004 each have complementary interior surfaces to receive the saw-tooth shaped non-planar compliant layer 1004. An end plate 1008 may be optionally provided to receive screws or another fixation device that may be used to fasten the intervertebral spacer 1000 to the vertebral bodies.

Figure 10A:
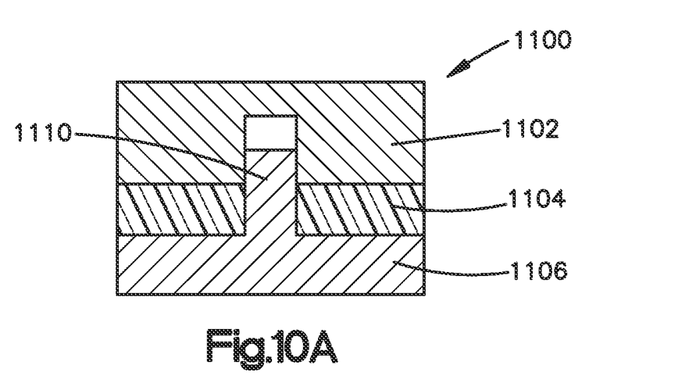
FIGS. 10A and 10B illustrate an intervertebral spacer in accordance with a ninth embodiment.
Figure 10B:
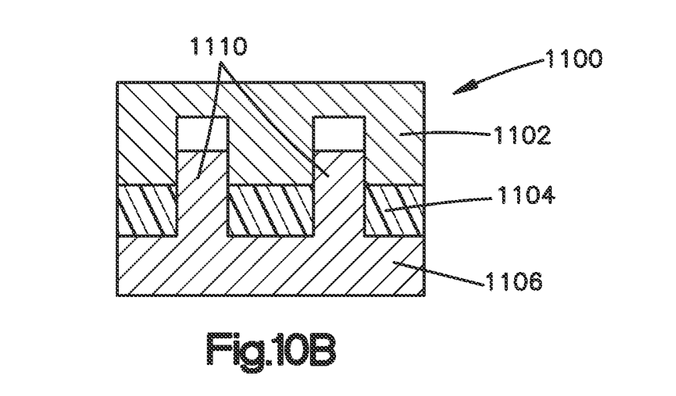

Referring now to FIGS. 10A and 10B, there is shown an intervertebral spacer 1110 in accordance with an eighth embodiment. As shown in FIG. 10A, a compliant layer 1104 is provided between a top surface of a lower layer 1106 and a bottom surface of an upper layer 1102. The lower layer 1106 includes a projection 1110 that is received within a cavity of the upper layer 1102. As shown in FIG. 10B, the lower layer 1106 may include plural projections 1110 to provide additional resistance to shear forces.

Figure 11:
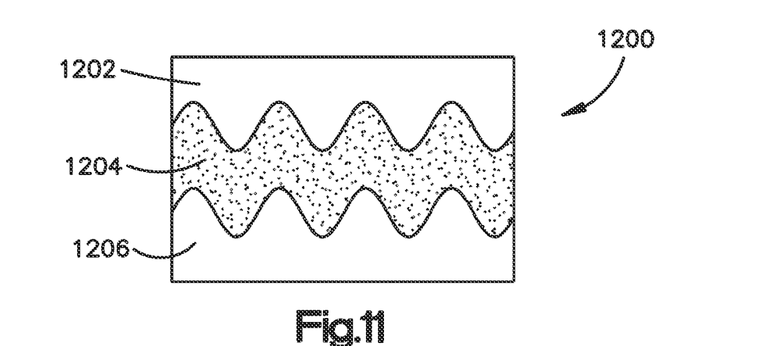
FIG. 11 illustrates an intervertebral spacer in accordance with a tenth embodiment.

Referring now to FIG. 11, there is shown an intervertebral spacer 1200 in accordance with a ninth embodiment. As shown, a non-planar compliant layer 1204 has a sinusoidal-shaped cross-section along the sides of the intervertebral spacer 1200. An upper layer 1202 and a lower layer 1206 each have a complementary interior surface to receive the sinusoidal shaped compliant layer 1204.

Figure 12A:
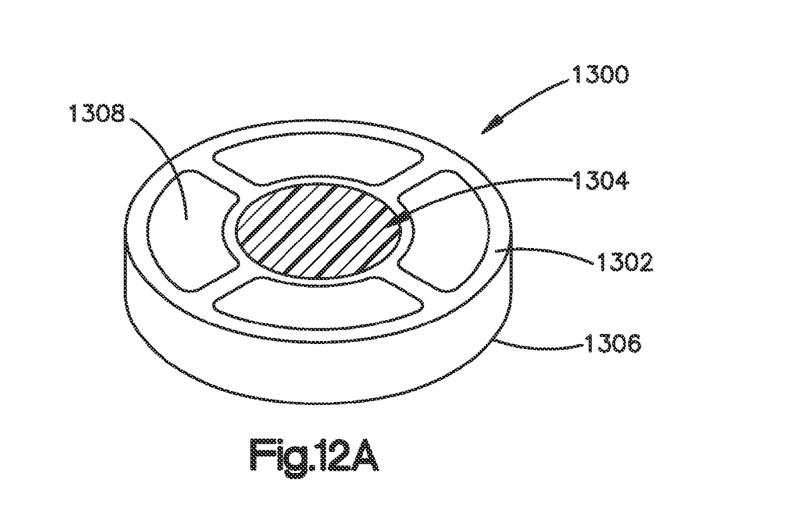
FIGS. 12A, 12B, and 12C illustrate an intervertebral spacer in accordance with an eleventh embodiment.
Figure 12B:
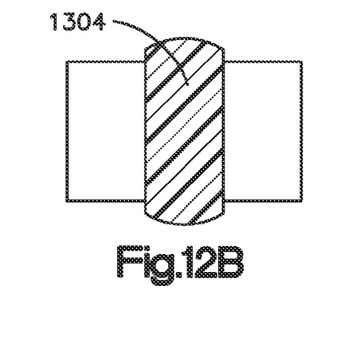
Figure 12C:
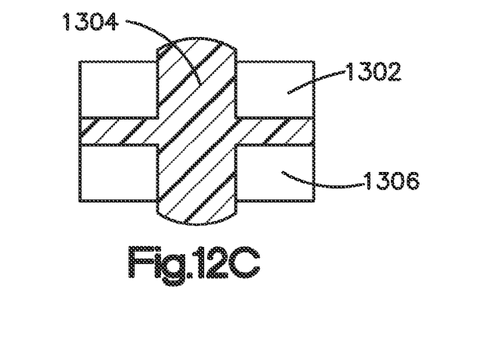

Referring to FIGS. 12A, 12B and 12C, there is shown an intervertebral spacer 1300 in accordance with an tenth embodiment. The tenth embodiment includes an upper layer 1302 and a lower layer 1306 each connected to a non-compliant layer 1304 in the shape of a central ring. As shown in FIG. 12B, within the non-planar compliant layer 1304 extends above and below the exterior surfaces of the upper layer 1302 and lower layer 1306, respectively, such that it is non-planar with respect to the horizontal axis of the intervertebral spacer 1300. In the example of FIG. 12C, the non-compliant layer 1304 may be connected to the upper layer 1302 and the lower layer 1306 by radial spokes.

Those skilled in the art will recognize that the method and system of the present invention has many applications, may be implemented in many manners and, as such, is not to be limited by the foregoing embodiments and examples. Any number of the features of the different embodiments described herein may be combined into one single embodiment and alternate embodiments having fewer than or more than all of the features herein described are possible. Functionality may also be, in whole or in part, distributed among multiple components, in manners now known or to become known. Moreover, the scope of the present invention covers conventionally known and features of those variations and modifications through the components described herein as would be understood by those skilled in the art. It is the intention, therefore, to be limited only as indicated by the scope of the claims appended hereto.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. An intervertebral spacer comprising:
an upper layer having a first exterior surface and a first interior surface;
a lower layer having a second exterior surface and a second interior surface;
a non-planar compliant layer substantially disposed between the first interior surface of the upper layer and the second interior surface of the lower layer,
wherein the first interior surface of the upper layer and the second interior surface of the lower layer each have a predetermined complementary shape to receive the non-planar compliant layer,
wherein the non-planar compliant layer includes a u-shaped portion along a cross-section thereof, and a leading portion and a trailing portion on opposite sides of the u-shaped portion, the leading portion and the trailing portion each having a planar inclined surface having its highest location most proximate the u-shaped portion and its lowest location farthest from the u-shaped portion, the first interior surface and the second interior surface each defining a corresponding leading portion and a trailing portion;
wherein the upper layer and lower layer comprise a first biocompatible material, and
wherein the non-planar compliant layer comprises a second biocompatible material that is more yielding than the first biocompatible material;
wherein the u-shaped portion comprises at least one island portion that is disposed within a recessed area of the lower layer, wherein the first interior surface includes a complementary protrusion that is received within the at least one island portion.

2. The intervertebral spacer of claim 1, wherein the non-planar compliant layer includes an other u-shaped portion along a cross-section thereof.

3. The intervertebral spacer of claim 1, wherein the intervertebral spacer is one of an oval-shaped, kidney-shaped, rectangular or trapezoidal shaped.

4. The intervertebral spacer of claim 1, wherein the intervertebral spacer comprises two sections for placement from a posterior side of a body.

5. The intervertebral spacer of claim 1, wherein the non-planar compliant layer comprises one of polyurethane, silicone, co-polymers of polyurethane, co-polymers of silicone, polyolefin, a foamed material, a material that cures in situ or that hardens over time, and polymer fibers formed as a woven structure.

6. The intervertebral spacer of claim 1, wherein the upper layer and lower layer comprise one of cobalt chrome, steel, titanium, titanium alloy, tantalum, zirconium, nitinol, alumina, zirconia, mixtures of alumina and zirconia, silicon nitride, Polyaryletherketone (PAEK), Polyether ether ketone (PEEK), polyether ketone ketone (PEKK), Poly Ether Ketone (PEK), polyether ketone ether ketone ketone (PEKEKK), Poly methyl methacrylate (PMMA), a carbon reinforced PAEK, or polyethylene.

7. An intervertebral spacer comprising:
an upper layer having a first exterior surface and a first interior surface;
a lower layer having a second exterior surface and a second interior surface;
a non-planar compliant layer substantially disposed between and engaging at least a portion of the upper layer and at least a portion of the lower layer, the non-planar compliant layer including a u-shaped portion along a cross-section thereof, and a leading portion and a trailing portion on opposite sides of the u-shaped portion, the leading portion and the trailing portion each having a planar inclined surface having its highest location most proximate the u-shaped portion and its lowest location farthest from the u-shaped portion, the upper layer and the lower layer each defining a corresponding leading and trailing portion;
wherein engagement of the non-planar compliant layer with the at least a portion of the upper layer and the at least a portion of the lower layer provides resistance to shear forces that act on the intervertebral spacer, and
wherein the upper layer and lower layer comprise a first biocompatible material, and
wherein the non-planar compliant layer comprises a second biocompatible material;
wherein the u-shaped portion comprises at least one island portion that is disposed within a recessed area of the lower layer, wherein the first interior surface includes a complementary protrusion that is received within the at least one island portion;
wherein the second biocompatible material is more yielding than the first biocompatible material.

8. The intervertebral spacer of claim 7, wherein the upper layer, the non-planar compliant layer and the lower layer define a pre-assembled unit having a geometrical shape.

9. The intervertebral spacer of claim 8, wherein the intervertebral spacer is one of an oval-shaped, kidney-shaped, rectangular or trapezoidal shaped.

10. The intervertebral spacer of claim 8, wherein the intervertebral spacer comprises two sections for placement from a posterior side of a body.

11. The intervertebral spacer of claim 7, wherein the non-planar compliant layer comprises one of polyurethane, silicone, co-polymers of polyurethane, co-polymers of silicone, polyolefin, a foamed material, a material that cures in situ or that hardens over time, and polymer fibers formed as a woven structure.

12. The intervertebral spacer of claim 7, wherein the upper layer and lower layer comprise one of cobalt chrome, steel, titanium, titanium alloy, tantalum, zirconium, niobium, nitinol, alumina, zirconia, mixtures of alumina and zirconia, silicon nitride, Polyaryletherketone (PAEK), Polyether ether ketone (PEEK), polyether ketone ketone (PEKK), Poly Ether Ketone (PEK), polyether ketone ether ketone ketone (PEKEKK), Poly methyl methacrylate (PMMA), a carbon reinforced PAEK, or polyethylene.

13. A multilayer intervertebral spacer, comprising:
a lower layer having a first engagement region having a first exterior surface and a first interior surface;
an upper layer having a second engagement region having a second exterior surface and a second interior surface;
at least one intermediate compliant non-planar layer having a portion thereof extending outside a lateral plane of the intervertebral spacer in which the at least one intermediate non-planar layer is disposed, the at least one intermediate layer engaging the first engagement region and the second engagement region, the at least one intermediate compliant non-planar layer including a u-shaped portion along a cross-section thereof, and a leading portion and a trailing portion on opposite sides of the u-shaped portion, the leading portion and the trailing portion each having a planar inclined surface having its highest location most proximate the u-shaped portion and its highest location farthest from the u-shaped portion, the upper layer and the lower layer each defining a corresponding leading and trailing portion;

wherein the at least one intermediate non-planar layer comprises a biocompatible material that is more yielding than that of the lower layer and the upper layer;

wherein the u-shaped portion comprises at least one island portion that is disposed within a recessed area of the lower layer, wherein the first interior surface includes a complementary protrusion that is received within the at least one island portion.

14. The multilayer intervertebral spacer of claim 13, wherein the intervertebral spacer is one of an oval-shaped, kidney-shaped, rectangular or trapezoidal shaped.

15. The multilayer intervertebral spacer of claim 13, wherein the at least one intermediate non-planar compliant layer comprises one of polyurethane, silicone, co-polymers of polyurethane, co-polymers of silicone, polyolefin, a foamed material, a material that cures in situ or that hardens over time, and polymer fibers formed as a woven structure.

16. The multilayer intervertebral spacer of claim 13, wherein the upper layer and lower layer comprise one of cobalt chrome, steel, titanium, titanium alloy, tantalum, zirconium, nitinol, alumina, zirconia, mixtures of alumina and zirconia, silicon nitride, Polyaryletherketone (PAEK), Polyether ether ketone (PEEK), polyether ketone ketone (PEKK), Poly Ether Ketone (PEK), polyether ketone ether ketone ketone (PEKEKK), Poly methyl methacrylate (PMMA), a carbon reinforced PAEK, or polyethylene.

* * * * *